(12) United States Patent
Rhee et al.

(10) Patent No.: US 8,859,811 B2
(45) Date of Patent: Oct. 14, 2014

(54) METHOD AND APPARATUS FOR RECOVERY OF AMINE FROM AMINE-CONTAINING WASTE WATER AND REGENERATION OF CATION EXCHANGE RESIN

(75) Inventors: In-Hyoung Rhee, Asan-si (KR); Hyun-Jun Jung, Suwon-si (KR)

(73) Assignee: Soonchunhyang University Industry Academy Cooperation Foundation, Asan-si (KR)

( * ) Notice: Subject to any disclaimer, the term of this patent is extended or adjusted under 35 U.S.C. 154(b) by 715 days.

(21) Appl. No.: 13/191,163

(22) Filed: Jul. 26, 2011

(65) Prior Publication Data

US 2012/0029233 A1 Feb. 2, 2012

(30) Foreign Application Priority Data

Jul. 27, 2010 (KR) .................. 10-2010-0072158

(51) Int. Cl.
*C07C 211/00* (2006.01)
*B01J 39/04* (2006.01)
*B01J 49/00* (2006.01)
*C02F 1/42* (2006.01)
*C07C 209/86* (2006.01)
*C02F 1/20* (2006.01)
*C02F 101/38* (2006.01)

(52) U.S. Cl.
CPC .............. *C02F 1/42* (2013.01); *B01J 39/043* (2013.01); *C02F 2209/02* (2013.01); *B01J 49/0008* (2013.01); *C02F 2303/16* (2013.01); *C02F 2001/425* (2013.01); *C07C 209/86* (2013.01); *C02F 1/20* (2013.01); *B01J 49/0069* (2013.01); *C02F 2301/063* (2013.01); *C02F 2101/38* (2013.01); *C02F 2303/10* (2013.01)

USPC ........................................... 564/1

(58) Field of Classification Search
CPC ............ C07C 2101/02; C07C 209/56; B01D 2311/04; B01D 2311/2653
USPC ........................................... 564/1
See application file for complete search history.

(56) References Cited

FOREIGN PATENT DOCUMENTS

WO    WO 2008013370 A1 *   1/2008

* cited by examiner

*Primary Examiner* — Sudhakar Katakam
*Assistant Examiner* — Kofi Adzamli
(74) *Attorney, Agent, or Firm* — Sughrue Mion, PLLC

(57) ABSTRACT

Provided is an apparatus for recovering amines from amine-containing waste water generated in power stations, etc., and regenerating a cation exchange resin. The apparatus includes: a cation exchange resin layer capturing amines from amine-containing waste water and eluting the amines therefrom; a degassing tower degassing the eluted amines; a vacuum pump connected to the degassing tower; and a condensation and cooling tower condensing the degassed amines at a temperature of −33° C. or lower, wherein the amines captured in the cation exchange resin layer are eluted by injecting a strong acidic solution, while the resin is regenerated, and the amines eluted by the strong acidic solution is subjected to vacuum degassing and then recovered. Provided also is a method for recovering amines and regenerating a cation exchange resin using the apparatus. The apparatus and method for recovering amines and regenerating a cation exchange resin improve the quality of effluent water from power stations, etc., and increase the cost-efficiency through the recycle of amines.

6 Claims, 1 Drawing Sheet

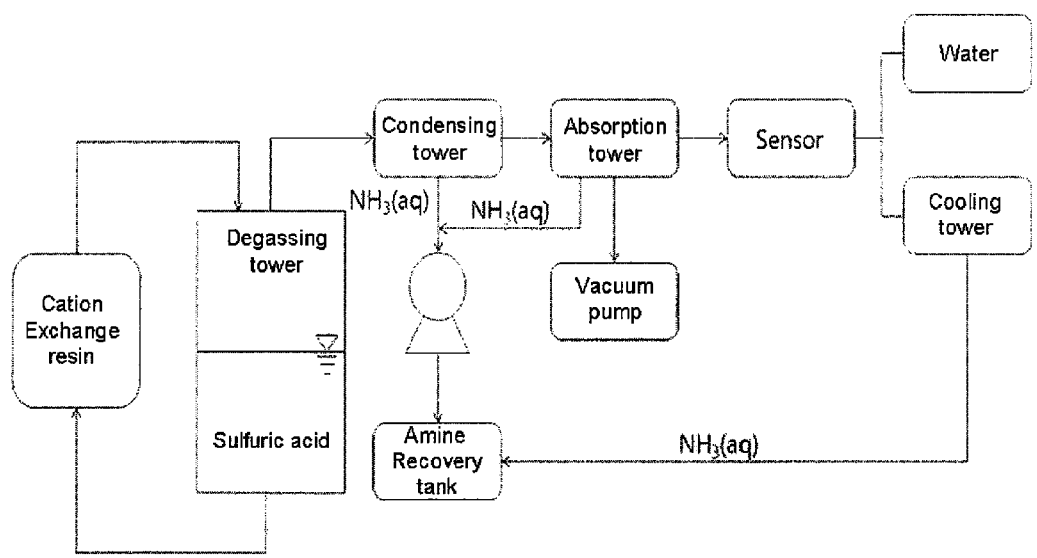

METHOD AND APPARATUS FOR RECOVERY OF AMINE FROM AMINE-CONTAINING WASTE WATER AND REGENERATION OF CATION EXCHANGE RESIN

CROSS-REFERENCE TO RELATED APPLICATION

This application claims priority to Korean Patent Application No. 10-2010-0072158, filed on Jul. 27, 2010, and all the benefits accruing therefrom under 35 U.S.C. §119, the contents of which in its entirety are herein incorporated by reference.

BACKGROUND

1. Field

This disclosure relates to an apparatus and a method for recovering amines with high concentration and high purity from amine-containing waste water generated from power stations, etc., and regenerating an cation exchange resin.

2. Description of the Related Art

In general, atomic force and thermal power stations use water as an energy transfer medium to obtain electric energy from atomic energy or fossil fuels. In such power stations, water steam vaporized from water is used generally to rotate a turbine, and electricity is generated through the rotation of the turbine. After rotating the turbine, water steam is condensed and reused.

While water steam is condensed, chemicals as a pH adjusting agent or an electrochemical potential controlling agent are introduced. Introduction of such chemicals is intended to inhibit various metals from electrochemical corrosion. In addition, power stations are provided and operated with an ion exchange resin tower for the purpose of circulation of water. In such an ion exchange resin tower, trace impurities as well as the chemicals introduced for the inhibition of corrosion are removed. Thus, power stations require the repetition of a process including introducing chemicals for each cycle of water/steam circulation, and then removing the chemicals with an ion exchange resin.

Among the chemicals introduced for each cycle of water/steam circulation, highly volatile compounds may be included and such compounds may be emitted to the air during the process. In addition, even after undergoing general physicochemical treatment processes, some ingredients, including amines, remain in water, resulting in an increase in COD and total nitrogen content. Under these circumstances, the waste water may not satisfy the effluent water quality standard.

SUMMARY

Disclosed herein is an apparatus for recovering amines from amine-containing waste water generated from power stations, etc., and regenerating an cation exchange resin.

Disclosed herein too is a method for recovering amines from amine-containing waste water and regenerating an cation exchange resin.

In one aspect, there is provided an apparatus for recovering amines from amine-containing waste water and regenerating an cation exchange resin, the apparatus including:

a cation exchange resin layer capturing amines from amine-containing waste water and eluting the amines therefrom;

a degassing tower degassing the eluted amines;

a vacuum pump connected to the degassing tower;

a condensation and cooling tower condensing the degassed amines at a temperature of −33° C. or lower; and an adsorption tower capturing at least one selected from the group consisting of water and amines, wherein the amines captured in the cation exchange resin layer are eluted by injecting a strong acidic solution, while the resin is regenerated as a hydrogen-form cation exchange resin, and the amines eluted by the strong acidic solution are subjected to vacuum degassing and then recovered.

In another aspect, there is provided a method for recovering amines from amine-containing waste water and regenerating a cation exchange resin saturated with ammonia, dimethyl amine, or the like, the method including:

converting an amine-form cation exchange resin into a hydrogen-form cation exchange resin by using a strong acidic solution;

degassing the eluted amines;

liquefying the degassed amines at a temperature of −33° C. or lower; and carrying out adsorption of water or amines to regenerate the cation exchange resin and recover the amines.

The method and apparatus for recovering amines and regenerating a cation exchange resin disclosed herein are capable of treating amines, which cause an increase in chemical oxygen demand (COD) and total nitrogen content from waste water of atomic force and thermal power stations, at the site where they are generated. Therefore, it is possible to prevent an increase in load of the existing waste water treatment plants and to avoid a need for improving the existing equipment. In addition, the amines, introduced continuously to prevent corrosion in water/steam circulation systems of atomic force and thermal power stations, can be recovered and reused, resulting in improvement of cost-efficiency in various power stations.

BRIEF DESCRIPTION OF THE DRAWINGS

The above and other aspects, features and advantages of the disclosed exemplary embodiments will be more apparent from the following detailed description taken in conjunction with the accompanying drawing in which:

FIG. 1 is a schematic view of the apparatus for recovering amines and regenerating a cation exchange resin in accordance with an embodiment of this disclosure.

DETAILED DESCRIPTION

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. Rather, these exemplary embodiments are provided so that this disclosure will be thorough and complete, and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In the drawings, like reference numerals in the drawings denote like elements. The shape, size and regions, and the like, of the drawing may be exaggerated for clarity.

In one aspect, the apparatus for recovering amines and regenerating a cation exchange resin in accordance with an embodiment of this disclosure is intended to regenerate a cation exchange resin saturated with highly volatile amines, such as ammonia, dimethyl amine, etc., and to recover amines from amine-containing waste water, the apparatus including:

a cation exchange resin layer capturing amines from amine-containing waste water and eluting the amines therefrom;

a degassing tower degassing the eluted amines;

a vacuum pump connected to the degassing tower;

a condensation and cooling tower condensing the degassed amines at a temperature of −33° C. or lower; and an adsorption tower capturing at least one selected from the group consisting of water and amines, wherein the amines captured in the cation exchange resin layer are eluted by injecting a strong acidic solution, while the resin is regenerated as a hydrogen-form cation exchange resin, and the amines eluted by the strong acidic solution are subjected to vacuum degassing and then recovered.

The amines introduced into the apparatus for recovering amines and regenerating a cation exchange resin pass through the cation exchange resin layer, in which volatile amines are captured. The amines captured in the exchange resin are eluted by introducing an acidic solution to the cation exchange resin layer. At that time, the resin saturated with amines is converted into a hydrogen-form cation exchange resin. The acidic solution is used as one capable of regenerating the cation exchange resin. Any acidic solution may be used, as long as it is capable of eluting the amines captured in the cation exchange resin layer, and particular examples of the acidic solution include sulfuric acid ($H_2SO_4$) and hydrochloric acid (HCl).

According to an embodiment, the apparatus may further include a storage tank in which a strong acidic solution is stored.

According to another embodiment, the cation exchange resin layer may include a cation exchange resin having a sulfonate group (—$SO_3H$) as an exchangeable group and divinylbenzene-styrene copolymer as a backbone. In addition, the ion exchange resin layer may be packed in a cylindrical tower structure made of a polymer material or metal, such as stainless steel. The tower structure packed with the ion exchange resin layer may include a polymeric material or metallic material, such as stainless steel, since such materials do not undergo corrosion even under a strong basic condition.

According to still another embodiment, at least one of the ion exchange resin layer and the condensation and cooling tower may include an adsorption layer that prevents gaseous amines from being emitted into the air. For example, the adsorption layer may include an ion exchange resin or zeolite packed therein. Such an ion exchange resin or zeolite has a lot of interstitial spaces, in which gaseous amines are adsorbed.

According to still another embodiment, the degassing tower may have a vacuum pump connected thereto. When the inner part of an evaporator is depressurized through the vacuum pump, it is possible to reduce the heating temperature required to evaporate amines. For example, the degassing tower may have an internal pressure of 700 mmHg or less, more particularly between 150 and 700 mmHg. The degassing tower may have a temperature of 150° C. or lower, more particularly between 25 and 150° C.

According to still another embodiment, the condensation and cooling tower may have a temperature of −33° C. or lower, more particularly between −50° C. and −33° C. Amines distilled from the degassing tower are recovered as liquid condensed at the condensation and cooling tower. More particularly, the condensation and cooling tower may include a condensation tower condensing amines and a cooling tower cooling the condensed amines. The condensation and cooling tower may further include an adsorption tower between the condensation tower and the cooling tower. For example, gaseous $NH_3$ passed through the condensation tower may be sent to the adsorption tower, and then directed to the cooling tower. Then, $NH_3$ cooled to −33° C. or lower at the cooling tower may be recovered and stored in the state of aqueous solution.

According to still another embodiment, the apparatus for recovering amines and regenerating a cation exchange resin may further include at least one of a gas/liquid separator and a gas/solid separator between the degassing tower and the condensation and cooling tower. For example, impurities and vapors generated during the depressurization and heating of low-purity amines at the degassing tower may be sent to the gas/liquid separator and/or gas/solid separator, before they are introduced into the condensation and cooling tower. Use of such a gas/liquid separator or gas/solid separator prevents organic materials and solids from being carried over and incorporated into the vapor phase. As used herein, the term "carry over" means a phenomenon in which non-volatile organic or inorganic materials fly into the atmosphere together with vapor or bubbles when a solution containing such organic or inorganic materials are boiled.

According to yet another embodiment, the apparatus for recovering amines and regenerating a cation exchange resin may further include am amine recovery tank in which the recovered amines are stored. The amine recovery tank allows the amines to be cooled and stored in a liquid state. Such liquid-state amines are easily stored and handled. More particularly, the amine recovery tank may be controlled to an internal temperature of 0° C. or lower. This is intended to increase the storability of the recovered amines and to maintain the amines in a liquid state.

In another aspect, there is provided a method for recovering amines from amine-containing waste water and regenerating a cation resin.

According to an embodiment, the method for recovering amines and regenerating a cation exchange resin is intended to recover amines from amine-containing waste water and to regenerate a cation exchange resin, the method including:

capturing amines from amine-containing waste water with the cation exchange resin and eluting amines therefrom;

degassing the eluted amines; and condensing the degassed gaseous amines at a temperature of −33° C. or lower, wherein the amines captured in the cation exchange resin are eluted by introducing a strong acidic solution, while the resin is regenerated and the eluted amines are subjected to vacuum degassing and then recovered.

According to another embodiment, when capturing amines from amine-containing waste water with a cation exchange resin and eluting amines therefrom, a strong acidic solution is introduced into the cation exchange resin in which the amines were captured. Any acidic solution may be used as long as it is capable of eluting the amines captured in the cation exchange resin, and particular examples of the strong acidic solution include sulfuric acid ($H_2SO_4$) and hydrochloric acid (HCl). The acidic solution induces ion exchange and regeneration of the cation exchange resin. While the resin is regenerated by capturing amines from amine-containing waste water with a cation exchange resin and eluting the amines therefrom, the original amine-containing waste water is highly concentrated and reduced in its amount. More particularly, the cation exchange resin may have a sulfonate group ($-SO_3H$) as an exchangeable group and divinylbenzene-styrene copolymer as a backbone.

After the cation exchange resin is regenerated by capturing amines from amine-containing waste water with a cation exchange resin and eluting the amines therefrom, the method may further include determining the purity of amines by measuring at least one of pH and electrical conductivity. Measurement of pH and/or conductivity allows separation of high-purity amines from low-purity amines. Then, the high-purity amines may be recovered and the low-purity amines may be further treated. More particularly, pH and conductivity may be used to determine the purity of amines; and amines having a pH of 8-12 and a conductivity of 0.01-4 ms/cm may be separated and recovered.

According to still another embodiment, in at least one of the operation of capturing and eluting amines and the degassing operation, it is possible to prevent gaseous amines from being emitted into the air through the use of an adsorption plate. For example, the adsorption plate may include an ion exchange resin or zeolite packed therein. Such an ion exchange resin or zeolite has a lot of interstitial spaces, in which gaseous amines are adsorbed.

According to still another embodiment, the degassing operation may be carried out under an internal pressure of 700 mmHg or lower, more particularly between 150 and 700 mmHg. For examples, amines eluted through the cation exchange resin are heated under a reduced pressure of 700 mmHg or lower. At that time, impurities and amine vapor are generated. When the degassing operation is carried out under reduced pressure, it is possible to reduce the heating temperature required to evaporate amines. For example, the degassing operation may be carried out at a temperature of 150° C. or lower, more particularly between 25 and 150° C. under the above-mentioned pressure range.

According to still another embodiment, the condensation operation may be carried out at a temperature of −33° C. or lower, more particularly between −50° C. and −33° C. Amines distilled from the degassing operation are recovered as liquid condensed at the condensation and cooling tower. More particularly, the condensation operation may include condensing the degassed amines, and cooling the condensed gaseous amines after being passed through an adsorption tower.

According to still another embodiment, the method for recovering amines may further include at least one operation of gas/liquid separation and a gas/solid separation before condensing the degassed amines. In this manner, it is possible to prevent organic materials and solids from being carried over and incorporated into the vapor phase.

According to yet another embodiment, the method for recovering amines may further include cooling and storing the recovered amines in a liquid state. In other words, the recovered amines are cooled and stored in a liquid state so as to facilitate storage and handling thereof. In certain embodiments, the liquid-state amines may be stored at a temperature of 0° C. or lower.

Hereinafter, one particular example of the apparatus and method for recovering amines and regenerating a cation exchange resin will be described.

Amines are captured from amine-containing waste water by using a cation exchange resin, and the captured amines are eluted and the waste water is concentrated. The elution of amines is performed by introducing an acidic solution (sulfuric acid, hydrochloric acid, etc.) to the cation exchange resin in which the amines are captured. In this manner, the cation exchange resin is regenerated. Then, the amines are subjected to degassing under reduced pressure or vacuum, the degassed amines are cooled to −33° C. or lower, and the cooled amines are recovered.

While the amine-containing waste water introduced to the apparatus is passed through the cation exchange resin, amines are captured in the cation exchange resin. Next, the captured amines are eluted by introducing an acidic solution to the amine-captured cation exchange resin. The eluted amines are depressurized and heated at a degassing tower, leading to the generation of impurities and amine vapor. The impurities are removed by a gas/liquid or gas/solid separator and the amine vapor is condensed. After the condensation, amines are recovered and the non-recovered portion of amines is adsorbed through an adsorption tower packed with a resin or zeolite. Finally, the recovered amines are cooled and stored in a liquid state at an amine recovery tank.

While the exemplary embodiments have been shown and described, it will be understood by those skilled in the art that various changes in form and details may be made thereto without departing from the spirit and scope of this disclosure as defined by the appended claims.

In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

What is claimed is:

1. A method for recovering amines from amine-containing waste water and regenerating a cation exchange resin, comprising:
    capturing amines from amine-containing waste water with the cation exchange resin and eluting amines therefrom;
    degassing the eluted amines; and
    condensing the degassed gaseous amines at a temperature of −33° C. or lower,
    wherein the amines captured in the cation exchange resin layer are eluted by introducing a strong acidic solution, while the resin is regenerated, and the eluted amines are subjected to vacuum degassing and then recovered.

2. The method for recovering amines according to claim 1, wherein the cation exchange resin have a sulfonate group ($-SO_3H$) as an exchangeable group and divinylbenzene-styrene copolymer as a backbone.

3. The method for recovering amines according to claim 1, wherein an adsorption plate is used to prevent the gaseous amines from being emitted into the air, when carrying out at least one of said capturing and eluting, and said degassing.

4. The method for recovering amines according to claim 1, wherein said degassing is carried out under a pressure of 700 mmHg or lower and a temperature of 150° C. or lower.

5. The method for recovering amines according to claim 1, wherein said condensing comprises condensing the degassed amines and cooling the condensed gaseous amines after being passed through an adsorption tower.

6. The method for recovering amines according to claim 1, wherein the recovered amines are cooled to and stored in a liquid state.

\* \* \* \* \*